United States Patent [19]

Underberg et al.

[11] Patent Number: 4,725,540

[45] Date of Patent: Feb. 16, 1988

[54] PROCESS FOR THE PREPARATION OF AMINE-OXIDASE CONTAINING MATERIAL, SO PRODUCED AMINE-OXIDASE CONTAINING MATERIAL

[75] Inventors: Emil Underberg, Dietlikon, Switzerland; Andreas Lembke, Eutin-Sielbeck, Fed. Rep. of Germany

[73] Assignee: Emil Underberg, Dietlikon, Switzerland

[21] Appl. No.: 750,877

[22] Filed: Jul. 1, 1985

[30] Foreign Application Priority Data

Jul. 9, 1984 [CH] Switzerland .................. 3321/84

[51] Int. Cl.$^4$ ............... C12P 39/00; C12N 9/06; C12R 1/225; C12R 1/72; C12G 1/00; A23K 1/00
[52] U.S. Cl. ............................. 435/42; 435/191; 435/853; 435/921; 426/52; 426/53; 426/12
[58] Field of Search ............... 435/42, 191, 259, 261

[56] References Cited

U.S. PATENT DOCUMENTS

| | | | |
|---|---|---|---|
| 2,289,194 | 7/1942 | Hiemenz | 435/191 |
| 3,990,944 | 11/1976 | Gauss et al. | 435/42 X |
| 4,410,625 | 10/1983 | Cadmus | 435/42 |
| 4,425,436 | 1/1984 | Matsumoto et al. | 435/191 |

OTHER PUBLICATIONS

Biochemical Journal, vol. 211, pp. 481–493 (1983).
Chemical Abstracts, vol. 63, 4587e (1965).
Chemical Abstracts, vol. 67, 51262c (1967).
Chemical Abstracts, vol. 82, 2803f (Cantoni et al.), (1975).
Chemical Abstracts, 99, 19342d, J. Green, "Serological differences . . . ", 1983.
Chemical Abstracts, 96, 100569t (1982), G. W. Haywood, "Microbial oxidation of amines . . . ".

Primary Examiner—Lionel M. Shapiro
Attorney, Agent, or Firm—Ladas & Parry

[57] ABSTRACT

A process for the preparation of histaminase, respectively a histaminase containing material, is described. Histaminase is a diamine-oxidase which metabolizes histamine.

According to the process at least one microorganism which produces in its cells histaminase, is cultivated and as soon as a sufficient number of microorganisms has grown, the microorganisms are isolated from the culture medium. Adhering culture medium is removed from the microorganisms and the microorganism cells are broken up and comminuted.

The product can be dried in the vacuum, cooled and stored or it can be used to produce products having a higher content of histaminase or to produce a pure histaminase.

Preferably a mixture of microorganisms is cultivated which contains at least one microorganism selected from the group lactobacillus and at least one yeast selected from the group candida.

The histaminase containing products, respectively the histaminase, are used for metabolizing histamine in foodstuffs, beverages and forages yielding corresponding histamine free products in which the histamine had been metabolized forming not harmful metabolization products.

15 Claims, No Drawings

4,725,540

PROCESS FOR THE PREPARATION OF AMINE-OXIDASE CONTAINING MATERIAL, SO PRODUCED AMINE-OXIDASE CONTAINING MATERIAL

TITLE OF THE INVENTION

Process for the preparation of amine-oxidase containing material, so produced amine-oxidase containing material and its use.

BACKGROUND OF THE INVENTION

It is well known in the art that many foodstuffs, forages and beverages contain histamine and some of said products have an undesired high content of histamine. Said products are mainly such products which were prepared according to a process which comprises at least one process step in which a conversion is performed by at least one microorganism. Examples for such products are products which were prepared by performing an alcoholic fermentation, like e.g. wine, sparkling wine, crackling wine, beer and distilled alcoholic beverages like e.g. brandy, as well as also products which were prepared by performing a lactic fermentation like e.g. sour milk products like yogurt, sour milk and curd, as well as also products that originate from plants which were as well submitted to a lactic fermentation, like e.g. pickled cucumbers, pickled cabbage (sauerkraut) and silo fodder. A further example of products which often have an undesired high content of histamine are several qualities of cheeses which were prepared by adding to milk rennet in order to recover a milk coagulate or starting from curd, in which processes for producing a cheese several fermentations, like e.g. lactic fermentations occur through which the curd or the milk coagulate is converted into the cheese.

In the naturally occurring microorganism population there are mainly present such microorganisms which metabolize any histidine present in the starting material forming histamine. This is the reason why products which were submitted to a conversion performed by a microorganism, like an alcoholic fermentation or lactic fermentation, usually have a rather high content of histamine, because the microorganisms which perform said lactic fermentation or alcoholic fermentation furthermore also metabolize histidine of the starting material forming histamine. If silo fodder containing histamine is fed to cattle then said histamine is transferred to the milk which is produced by the cow.

It is well known in the art that histamine is noxious for many persons, specially such persons which suffer from allergies. It was the object of the present invention to produce an amine-oxidase containing material, respectively amine-oxidase. A further object of the present invention was to use said amine-oxidase containing material for removing enzymetically histamine from foodstuffs, beverages and forages.

DESCRIPTION OF THE PRIOR ART

In the British Pat. No. 2 031 948 there is described a process for the preparation of foodstuffs, beverages and forages which have a drastically lower histamine content or are completely free of histamine. Some of the microorganisms strains present in the naturally occurring microorganism population and some of the microorganism strains which are already deposited for a long time in culture collections metabolize histidine without forming histamine. According to the process described in said British patent, specifically such single cell cultures of microorganisms are used for the preparation of foodstuffs, beverages and forages which metabolize histamine without forming histidine. Either the conversion performed by a microorganism is specifically performed according to said process by performing said conversion, like an alcoholic fermentation or lactic fermentation with such single cell cultures of microorganisms which metabolize histidine without forming histamine, or if a product having only a low content of protein is prepared, like e.g. an alcohlic fermentation is made, the histidine present in the starting material is removed from said starting material using microorganism strains which metabolize said histidine without forming histamine and the so prepared intermediate product which is already free of histidine is thereafter submitted to the conversion using any desired microorganism strains, including such strains which would metabolize any histidine present forming undesired histamine. According to said process, e.g. to a sterilized must such a lactobacillus strain is added which performs a lactic fermentation and, furthermore, metabolizes any histidine present without forming histamine, and thereafter the intermediate product which is free of histidine, is submitted to an alcoholic fermentation using any desired kind of yeast in order to produce a wine. According to the process described in said British patent, the metabolization of the histidine without forming histamine, can also be made using an enzyme which has been recovered from such a microorganism strain which metabolizes histidine without forming histamine.

The disadvantage of the process described in said British patent is that any histamine which is already present cannot be removed. According to said process only the degradation of histidine to histamine can be prevented. If. e.g. a histamine containing silo fodder is fed to cows, the produced milk contains already some histamine. According to the process of said British patent, the lactic fermentation of said milk can be performed so that no further histidine of the milk is degraded by the microorganism strain performing the lactic fermentation to form histamine. Accordingly, the so produced sour milk product has no higher content of histamine than the fresh milk used for its preparation. However, the histamine which was already present in the used fresh milk is not removed by the microorganism strain which performs the lactic fermentation.

It is furthermore known in the art that histaminase, i.e. a histamine degradating enzyme is present in the blood serum of mammalia, e.g. in the serum of pigs, and said histaminase can be also found in the kidney tissue of mammalia. For instance in the U.S. Pat. No. 2,289,194, there is described a process for preparing a stable histaminase preparation from hog kidneys in which the finely minced kidneys are submitted to several extracting steps and precipitating steps.

In the French patent publication No. 2 101 095 there is described a process for preparing a diamine-oxydase containing preparation starting from human placenta.

All the prior art processes according to which histaminase or a histaminase containing product is isolated from tissues of mammalia or the blood serum of mammalia, however, suffer from the disadvantage that the isolation is rather complicated and comprises usually many purification steps like dialysis, several extractions, precipitations and so on.

In the publication "Chemical Abstracts", volume 99, no. 3, page 343, abstract 19342d of July 18, 1983, there are described Serological differences between the multiple amine oxidases of yeasts. Furthermore, the purified enzymes isolated from the microorganisms candida utilis and the microorganism Pichia pastoris are compared and the oxidation of some amines and the amino acids lysine and ornithine using said amine oxidase was investigated. There cannot be taken from said abstract a reference whether or not histidine is degradated by said amine oxidase.

In the "Chemical Abstracts", volume 96, no. 13, page 382, abstract 100569t of Mar. 29, 1982, the microbial oxidation of amines is investigated. The properties of two primary-amine oxidases which were isolated from the microorganism strain candida boidinii were tested, however, also from said publication no reference can be taken whether the corresponding amine oxidases degradate histamine or not.

In the German Offenlegungsschrift No. 3 206 826 a process for the preparation of amine-oxidase by cultivating amine-oxidase producing microorganisms is described. Specific microorganism genera are used for performing said process, i.e. microorganisms of the genera talaromyces, eupenicillium, petromyces, neosartorya and eurotium.

SUMMARY OF THE INVENTION

The object of the present invention was a simple process for the preparation of an amine-oxidase containing material by cultivating microorganisms and using the corresponding destroyed and diminuted microorganism cells or a product isolated therefrom as material for degradating histamine. The product of the inventive process will be used for removing histamine from foodstuffs, beverages and forages.

It was unexpectedly found out that the desired amine-oxidase was contained in the cultivated microorganisms themselves while the culture medium is essentially free of said enzymes. It, furthermore, was quite unexpectedly found out that a specially preferred microorganism for producing the desired amine-oxidase containing material is a mixed microorganism culture which contains at least one microorganism selected from the group lactobacillus and, furthermore, at least one yeast selected from the group candida.

DESCRIPTION OF THE INVENTION

The object of the present invention is a process for the preparation of amine-oxidase containing material in which process at least one microorganism which produces in its cells a D(—)-amine-oxidase is cultivated in a nutrient medium and as soon as a sufficient number of microorganisms has grown, said microorganisms are separated from the culture medium and any remaining culture medium which is adhering to the microorganisms is removed by washing or by suspending the isolated microorganisms in a liquid medium and separating them again from said liquid medium and wherein the microorganism cells are thereafter diminuted or crushed.

According to said process a material is isolated which contains a histaminase, i.e. a diamine-oxidase. Said oxidase is a pyridoxalphosphate containing oxidase which oxidates in the presence of oxygen e.g. at pH-values in the range of 6.7–7.6 histamine forming ammonia, hydrogen peroxide and amino-aldehydes. Said degradation of the histamine, therefore can be performed about in the neutral pH-range and, accordingly, with said histaminase containing product also such materials can be freed of histamine in which the adjustment of an acid pH-range has to be avoided, because said products are deteriorated under acid conditions, like e.g. fresh milk.

It can be seen from the above explanation that the histaminase containing material prepared according to the inventive process, contains a corresponding D(—)-amine-oxidase.

In the present description the terms "histaminase", respectively "diamine-oxidase", respectively "D(—)-amine-oxidase" are used and all said terms indicate that a corresponding ferment or enzyme is concerned with which histamine can be metabolized.

It is, furthermore, also known in the art that "D(—)-amine-oxidase" are to be found in the peroxysomes of the liver, i.e. the so called microbodies of the liver, and in said peroxysomes there are furthermore also present catalases which perform the metabolization of the hydroperoxide which has been formed by said oxidases. As already outlined above, the isolation of said "D(—)-amine-oxidase" from the liver is as difficult and time-consuming as the isolation of such an enzyme material is from any desired animal tissue.

Contrary to this, the inventive process makes it possible to produce a material which contains diamine-oxidases and degradates histamine in a simple way. This makes it possible to produce the histamine degradating material in a simple and cheap way and, furthermore, in the required large quantities so that the histaminase containing product can be used for destroying any histamine which is contained in foodstuffs, beverages and forages.

When the inventive process is performed and at least one microorganism is cultivated in a suited nutrient medium, then quite unexpectedly the desired D(—)-amine-oxidase is formed in the microorganisms and not liberated into the culture medium in any essential degree. Therefore, accordingly, as soon as the necessary amount of microorganisms has grown in the nutrient medium, it is only necessary to remove from said microorganisms any adhering culture medium, i.e. by washing or by suspending them again in a liquid medium and isolating them again, and thereafter the so purified microorganism cells are diminuted, e.g. homogenized, crashed or minced and said damaged microorganism cells can be used as such as the amine-oxidase containing material for destroying any histamine in beverages, foodstuffs or forages.

It can be assumed that the histaminase is not liberated into the culture medium because it is obviously bonded to the protoplasm of the cultivated microorganisms. In order that the histaminase contained in the isolated microorganism cells can be actually used for degradating the histamine, it therefore is necessary that the cells are opened, i.e. destroyed or disrupted. The histaminase containing product prepared according to the inventive process, accordingly, should be essentially free of any not damaged microorganism cells.

Preferred microorganisms which are used in the inventive process for producing the diamine-oxidase containing product are microorganisms of the class of fungi, the class of bacteria or the class of yeasts. Specially preferred bacteria are bacteria which metabolize sugar constituents of the nutrient medium forming lactic acid. Specially preferred yeasts are yeasts of the group candida.

If in the inventive process for the preparation of the histaminase containing material such bacteria producing lactic acid like mutants of *Lactobacillus delbrueckii* or *Lactobacillus leichmannii* are used then large numbers of cells have to be cultivated, because the above state microorganisms produce histaminase and, furthermore, also transaminase and desaminase. A large number of microorganism cells, accordingly, is necessary in order that sufficient histaminase containing material is obtained. The above stated strains of microorganisms metabolize glucose and other carbohydrates contained in the nutrient medium in a homofermentive way forming D(−)-lactic acid.

According to a preferred embodiment of the inventive process the histaminase containing material is produced by cultivating a mixed culture comprising at least one microorganism selected from the group lactobacillus and at least one yeast selected from the group candida. Preferably the cultivation in said mixed microorganism culture is performed under such cultivation conditions, respectively such specific microorganism strains are selected for performing said mixed cultures that the lactobacillus in question metabolizes sugar constituents of the substrate forming lactic acid, while the used candida species metabolizes the produced lactic acid, however not the sugar constituents which are present in the nutrient medium. In said mixed microorganism cultures, accordingly, the sugar constituents of the nutrient medium are first metabolized by the lactobacilli forming lactic acid and said lactic acid is the carbon source for the yeast which further metabolizes said lactic acid. A further advantage of the use of said mixed microorganism culture is the following: The microorganisms contain histaminase and they, accordingly, metabolize histamine as outlined above liberating ammonia. The yeast present in said mixed culture, i.e. the candida species, uses said liberated ammonia for synthesizing the proteins of the yeast. Accordingly, in said mixed microorganism culture the used microorganisms are able to consume the constituents of the nutrient medium in an optimal way.

If a mixed culture of at least one micororganism selected from the group lactobacillus and at least one yeast selected from the group candida, is grown in order to produce the histaminase containing material according to the inventive process, then attention has to be paid that the microorganism strains are selected so that the optimal growth conditions are as similar as possible. Accordingly, the optimal cultivation temperature, the optimal pH-value of the culture medium and similar parameters should be in about the same range for the at least two selected microorganism strains.

Paying attention to the above requirements, as specially preferred mixed microorganism culture, used in the inventive process for the preparation of the histaminase containing product is a culture in which the strain *Lactobacillus bulgaricus* and the strain *Candida crusei* is cultivated.

A preferred cultivation medium for the cultivation of a mixed microorganism culture containing at least one microorganism selected from the group lactobacillus and at least one microorganism selected from the group candida is an aqueous medium which contains the sugar constituent lactose. Because of economic reasons aslactose containing nutrient medium there is preferably used whey, preferably whey having a reduced protein content or whey which is completely free of proteins. If such a deproteinized whey is used as nutrient medium for the cultivation of the mixed microorganism cultures then at the beginning of the cultivation a yeast autolysate is added.

According to a preferred embodiment for performing said cultivation of the mixed microorganism culture two fermentation vessels are used. After a starting phase of the cultivation into the first fermenter the whey is supplied maintaining a constant admission rate. In the first fermenter the lactic bacteria and the yeasts contained therein are cultivated maintaining a limited supply of air. Said limited supply of air is required in order to insure that all the lactose contained in the whey is completely converted into lactic acid. When the growth of the yeasts starts in the first fermenter then said yeasts consume from the nutrient medium mainly lactic acid. In the further cultivation phase, the main growth phase, which is performed in the second fermenter, the yeasts consume also ammonia. For the growth of the yeasts nitrogen containing material has to be supplied. In the first fermenter the amount of nitrogen containing material present is generally so that the percentages of yeasts and percentages of lactic bacteria remain about constant.

In the first fermenter the pH-value of the nutrient medium is controlled and maintained constant by adding ammonia.

Also in the second fermenter the pH-value is continuously measured and maintained constant, however in said second fermenter the regulation of the pH-value is performed indirectly by controlling the supply of air in the first fermenter.

The above described cultivation procedure enables the maintaining of optimal growth conditions in the cultivation medium for the mixed microorganism cultivation. Thereby an optimal ratio of the intermediately formed product, i.e. ammonium-lactate to lactic acid is adjusted and said intermediate products are consumed as carbon source continuously from the yeasts present in the culture.

Contrary to the first fermenter, however, in the second fermenter no limited air supply is maintained but the optimal air required is supplied.

As already explained above, the cultivation of said mixed cultures of lactic bacteria and yeasts makes it possible that all the lactose present in the nutrient medium is converted by the lactic bacteria into lactic acid, because in the culture medium there are not reached too high concentrations of lactic acid because said lactic acid is continuously metabolized by the yeasts present in said culture medium. At the end of the cultivation usually no more lactose can be detected in the nutrient medium and said optimal consumption of the used nutrient medium is most advantageously achieved by performing a continuous cultivation.

Performing the inventive process preferably one or more microorganism strains are cultivated which are selected from the following classes of microorganisms: *Lactobacillus delbrueckii, Lactobacillus leichmannii, Lactobacillus bulgaricus* and *Candida crusei*. If the inventive process is performed by cultivating a mixed culture of a lactobacillus species and a candida species, then a specially preferred mixed culture is the one in which simultaneously *Lactobacillus bulgaricus* and *Candida crusei* are cultivated. The temperature in the fermenter or the fermenters should be maintained in the range of 42°–46° C., preferably at about 44° C., and the pH-value of the cultivation medium should be maintained constant in the range of 5.0–5.5.

As soon as a sufficient number of microorganisms has grown, said microorganisms are separated from the cultivation medium and any adhering culture medium is removed from the isolated microorganisms, e.g. by washing or by suspending the isolated microorganisms again in a liquid medium and separating them again from said medium. Thereafter the microorganism cells are destroyed by diminuting the microorganism cells in any desired way like e.g. smashing or crashing them or by treating them in a homogenizer.

According to one embodiment of the inventive process from the destroyed microorganism cells there is directly prepared a storable enzyme preparation containing D(−)-amine-oxidase by drying the diminuted microorganisms in the vacuum, preferably at a temperature of less than 7° C. It is specially preferred to perform said drying operation at a temperature of +4° C.

The working steps described below are advantageous because they allow a simple isolation of the microorganisms from the culture medium and an easy production of a storable enzyme product containing histaminase.

After the cultivation the microorganisms contained in the culture medium are isolated by centrifuging, e.g. centrifuging with 15,000 to 25,000 g. This yields a mass of cells which is cooled to +4° C. One part by weight of said centrifuged mass of cells were introduced into 8–12 parts by weight of a physiological brine solution, and the microorganism cells are again suspended in said solution. Thereafter the microorganism cells are again separated, preferably by centrifuging, preferably under the same conditions as described above for the isolation of the microorganism cells from the culture medium. The so recovered mass of cells is then diminuted, e.g. homogenized and dried under vacuum, preferably lyophilized. This yields a storable raw enzyme product containing histaminase. If said raw product is introduced into an aqueous 0.2 molar acetate puffer having a pH-value of 4.9, then it metabolizes histamine.

According to another embodiment of the inventive process the microorganism cells are first isolated according to the above stated process and also freed of the adhering culture medium by first suspending them again in a physiological brine solution and separating them again by centrifuging according to the above described processes. One part of volume of said purified mass of cells is then mixed with 3–6 parts of volume of acetone and said mixture is cooled and stirred until it coagulates and a sediment is precipitated. Said stirring and sedimentation process is preferably performed at a temperature of less than +7° C., e.g. at a temperature of about +4° C.

Thereafter the supernatant liquid material is removed and the remaining residue filtered and the filter cake washed thoroughly. Preferably the filter cake is first washed with a water mixable organic solvent which is easily evaporable, like e.g. acetone, and thereafter the filter cake is washed with an organic solvent that can be as well easily evaporated, like e.g. diethyl ether. After the last washing procedure the product is again isolated by suction filtration and dried without any application of heat. For example the product can be first dried in the air and thereafter in the vacuum over concentrated sulphuric acid. In order to provide a product with a good storability, it is essential that a careful drying is performed and that, furthermore, the product is stored under dry conditions, preferably at a temperature of not more than +7° C.

According to a further embodiment of the inventive process the microorganism cells contained in the culture medium are isolated by centrifuging. Thereafter the centrifuged mass of cells is freed of any adhering culture medium by resuspending said mass of cells in a physiological brine solution and isolating thereafter the microorganism cells again by centrifuging. Said mass of cells is then diminuted, preferably at a temperature of less than 7° C., e.g. at a temperature of +4° C. It is essential that the cells are diminuted so that very small cell debris are formed. Therefore, usually the cells are homogenized using a corresponding homogenizer.

According to one embodiment the mass of the finely diminuted cell debris is then treated with an extraction fluid, for instance an aqueous solution containing 0.85% by weight of sodium chloride yielding a raw enzyme solution.

According to another possible procedure from the finely divided cell debris the juice is squeezed off and said juice is cooled, preferably to a temperature of +5° C. and immediately ammonium sulphate is added, preferably until a concentration of 25% ammonium sulphate is reached. Thereby a precipitate is formed which is removed by centrifuging and said precipitate is discarded. To the supernatant liquid which is kept cool, preferably at a temperature of +5° C., there are added further quantities of ammonium sulphate until a content of 55% of ammonium sulphate is reached in said aqueous medium. Said second precipitation yields a sediment which contains the histaminase. The sediment is isolated by centrifuging and dried in the vacuum using a drying agent. The dried product is thereafter milled and said dry enzyme powder stored.

From the crude emzyme solution which was prepared according to the above stated process, the different enzymes can be isolated by using a chromatographic column. Suitable fillings for said column are Sephades of G-type, like for example Sephadex G-25 and, furthermore, DEAE-Sephadex A-50. Also cation exchangers are suitable filling materials for the chromatographic column, like e.g. carboxymethylcellulose.

Accordingly, one possible isolation procedure comprises a first step an application of the raw enzyme solution onto a column which is filled with Sephadex G-25. After the enzyme solution has passed said column the recovered product is an enzyme preparation which is free of salts. For the further purification of said salt-free enzyme preparation, there can be used a column which is filled with DEAE-Sephadex or a column which is filled with carboxymethylcellulose.

If a column filled with carboxymethylcellulose is used, then it is advantageous to equilibrate the filling of said column first with a suitable buffer solution. Thereby attention has to be paid that the pH-value of said buffer solution is shifted more to the acidic range for 0.5 pH-steps to 1 pH-step than the isoelectric point of the protein which will be separated.

After the column which is filled with carboxymethylcellulose had been equilibrated, the application of the enzyme solution onto said column is performed. The elution is made with buffer solution which has a higher pH-value than the buffer solution which was used for equilibrating the column. For the elution there can be used a series of buffer solutions in which the pH-value is sequentially higher from one buffer solution to the next one. According to an alternate procedure the elution is performed with a series of buffer solutions in which each has the same pH-value, in which series, however, the salt content of the used buffer solutions is sequentially increased. The used buffer solutions can be any desired anionic buffers, like e.g. an acetate containing puffer or a phosphate containing buffer.

A further object of the present invention is a diamine-oxidase containing product or a product consisting of diamine-oxidase which was prepared according to the inventive process.

Said diamine-oxidase, i.e. histaminase containing products or products consisting of histaminase will be preferably used for removing histamine of foodstuffs, beverages and forages.

A further object of the present invention, accordingly, is the use of said product which contains diamine-oxidase or consists of diamine-oxidase for degrading histamine in foodstuffs, beverages and forages.

According to a preferred embodiment of said use, foodstuffs or forages which are in the liquid state are first treated with the product containing the diamine-oxidase or consisting of the diamine-oxidase in order to remove from said product any histamine. According to said process the product which contains the histaminase or consists of the histaminase is added to the foodstuffs or animal feed which is in the liquid state. After a certain time of contact a colorimetric test procedure which is well known in the art is used in order to examine whether the liquid foodstuffs, respectively liquid animal feed is already free of histamine.

When said test procedure shows that the histaminase has already metabolized all the histamine, optionally the histaminase can be desactivated by heating the liquid foodstuffs or animal feed. In general, however, such a heating step does not need to be performed because usually the histaminase is desactivated by and by while it is in contact with the liquid foodstuffs or animal feed so that after a lapse of time no further treatment has to be performed in order to desactivate said histaminase.

From the liquid foodstuffs or forages which was freed of any histamine by contacting it with the histaminase containing products or the products consisting of histaminase, thereafter there can be prepared a solid or semisolid foodstuff or forage.

As already outlined above, fresh milk usually already contains histamine because the cows were fed with a histamine containing silo fodder and the body of the cow transferred said histamine which was taken up with the fodder, into the milk. The histamine contained in such a fresh milk can be removed by contacting said milk with an inventive product which contains histaminase or consists of histaminase and said contacting can e.g. be performed maintaining a pH-value which is about 7. Thereafter from said milk in the usual way there can be produced a milk coagulate by adding rennet and said milk coagulate for instance can be used for producing a cheese. The milk coagulate and, furthermore, also the whey from which it is separated are, accordingly, free of histamine and this is specially important if the whey is used for producing a beverage on whey basis or if the whey is used as animal feed.

Using the products preparted according to the inventive process which products contain histaminase or consist of histaminase, histamine can be also degraded in the acidic pH-ranges, e.g. at pH-values in the range of 4-5. Accordingly, the products prepared according to the inventive process can be also used to remove histamine from beverages having an acidic pH-value, e.g. from corresponding alcoholic beverages like wine.

The inventive process, the products prepared according to the inventive process and their use for removing histamine, will be further illustrated with the following examples. Said examples, however, in no way will limitate the scope of the claimed invention.

EXAMPLE 1

Preparation of histaminase containing products by cultivating bacteria which produce lactic acid.

The used microorganisms were mutants of *Lactobacillus delbrueckii* or *Lactobacillus leichmannii*. The above stated strains or microorganisms metabolize glucose, other sugar constituents or other carbohydrates in the homofermentative way producing D(−)-lactic acid. Both above stated microorganism strains form histaminase and, furthermore, also transaminases and desaminases. With transaminases and desaminases, histamine cannot be degradated, but transaminases and desaminases only can be used to degradate histidine present in the starting material without forming histamine. It, however, is in no way disadvantageous if the final product which is produced by the cultivation of the microorganisms contains in addition to histaminase, i.e. the diamine-oxidase, furthermore also transaminases and/or desaminases. Attention, however, has to be paid that a sufficient quantity of microorganisms is cultivated, in order that a sufficient quantity of the final product containing the histaminase is produced.

For the cultivation of the above stated mutants of lactobacillus, the lactobacillus-bouillon of De Man, Rogosa and Sharp can be used and said nutrient medium yields good results.

The composition of said nutrient medium is stated in the following table:

| Component | quantity in g/l |
|---|---|
| peptone | 10 |
| meat extract | 8 |
| yeast extract | 4 |
| dextrose | 20 |
| di-potassium hydrogenphosphate | 2 |
| sodiumacetate.3 H$_2$O | 5 |
| tri-ammonium citrate | 2 |
| magnesiumsulfate.7 H$_2$O | 0,2 |
| manganesesulfate.4 H$_2$O | 0,05 |

As further component said nutrient medium contains the surfactant Tween 80 in an amount of 1 ml/l medium.

The pH-value of said medium was adjusted to 6.2±0.1.

Thereafter the nutrient medium was inoculated by introducing a rather high number of one of the above stated microorganism strains of lactobacillus and the medium was maintained at a temperature of 37° C. The medium, thereafter, was incubated for three days at 37° C. maintaining anaerobic conditions by adding a material that generates carbondioxide.

After three days a sufficient reproduction of the microorganism cells was observed and the cells were isolated from the nutrient medium by centrifuging with about 20,000 g. The mass of cells was recovered and immediately cooled to +4° C.

Said mass of cells was then again suspended in a physiological brine solution by suspending one part by weight of said mass of cells in 10 parts by weight of the physiological brine solution. The microorganism cells were isolated from said suspension by centrifuging in the same way as outlined before, i.e. with about 20,000 g.

The recovered mass of cells was comminuted and dried in the vacuum by freeze-drying. Attention was paid that the product was actually completely dry.

The so prepared freeze-dried product was stored at a temperature of not more than +4° C. With said product histamine can be metabolized in a 0.2 molar acetate puffer solution having a pH-value of 4.9.

If the product is stored for several weeks at a temperature of not more than +4° C., it maintains its enzymatic activity.

EXAMPLE 2

The lactobacillus strains of example 1 were cultivated in the same way as described in example 1 and the microorganism cells were isolated from the culture medium by centrifuging as described in example 1 and, thereafter, they were again suspended in a physiological brine solution and isolated by centrifuging according to the process described in example 1.

The so recovered mass of cells was diminuted and cooled to a temperature of 4° C. One part per volume of said cell mass was mixed with 5 parts by volume of acetone having a temperature of 4° C. and the cold mixture was stirred until the coagulation occurred. Thereafter the mixture was left in the cold until the sediment had precipitated and the supernatant acetone was discarded. The residue was collected by suction filtration using a Buchner-funnel. The suction operation was performed carefully in order to prevent any cracks forming in the filter cake. This is an important feature because if any cracks expand through the filter cake then with the following washing operation no sifficient purification of the filter cake could be achieved.

The filter cake was washed twice with acetone and once with diethylether, the solvent was sucked off carefully, the filter cake comminuted and submitted to a predrying at the air.

After said predrying step in the air, the product was further dried in vacuum over a moisture absorbing agent, like concentrated sulphuric acid. The product was stored in a desiccator at a temperature of +4° C. It is essential that the drying step is performed thoroughly and that the product is stored under moisture free conditions in order that any deterioration of the product during the sotring is prevented.

EXAMPLE 3

According to the process described in example 1 the mutant of the *Lactobacillus delbrueckii* was cultivated and the isolation of the microorganism cells from the cultivation medium was performed as in example 1. Also the resuspending of the cell mass which was recovered by centrifuging in the physiological brine solution and the second centrifuging of the cells in order to recover them from the brine solution were performed in the same way as described in example 1. The mass of cells was thereafter cooled. It then was comminuted to very fine particles at a temperature of 4° C. using a homogenizer.

The homogenizing of the mass of cells was performed using a Potter-Elverhjem homogenizer. Said homogenizer is equipped with a mechanically rotating pestle which is pressed in a cylindrical glass vessel so that only a small gap of about 0.25 mm is maintained between the pestle and the glass vessel. The microorganism cells are mechanically ground in said gap between the pestle and the wall of the glass vessel. The pestle can be moved with the motor of a stirrer which rotates with about 1000 rpm. The cylindrical glass vessel is, furthermore, moved up and down while the pestle is maintained in a constant height. Said homogenizer makes it possible to comminute the microorganism cells forming very fine cell particles.

After said homogenizing of the cells there is squeezed off of the cells in a press device the juice of the cells. Said juice is maintained in a container at 5° C. and immediately ammonium sulfate is added until a 25% saturation of the juice with ammonium sulfate is reached. A precipitate is formed and the suspension is centrifuged.

The supernatant liquid material is recovered while the precipitate is discarded. The liquid material is maintained at a temperature of 5° C. and further quantities of ammonium sulfate are added until a saturation of 55% is reached. Thereby again a precipitate is formed which is recovered by centrifuging. Said solid material is carefully dried under vacuum over a moisutre absorbing material, preferably $P_2O_5$.

The dried product is ground to powder and said powder stored under moisture free conditions at 4° C. After a storing period of two months with said powder histamine can be completely metabolized.

EXAMPLE 4

The microorganism strain *Lactobacillus leichmannii* used in example 1 was cultivated in the same way as described in example 1 and the microorganism cells were thereafter isolated from the culture medium by centrifuging as described in example 1. Furthermore, said cells were freed of the culture medium adhering to them by suspending them in physiological brine solution and recovering them by centrifuging once again as described in example 1.

The comminution of the so produced mass of cells was performed according to the process described in example 3 using the homogenizer of Potter-Elverhjem.

During the homogenization of the cells or after their homogenization an aqueous sodium chloride solution containing 0.85% sodium chloride is added as extraction medium, preferably in a quantity of 1 to 2 parts by weight of said sodium chloride solution per part by weight of the homogenized cells.

The resulting crude enzyme solution can be directly used for degradating histamine in a beverage or a liquid foodstuff or forage.

The above stated raw enzyme solution can be further purified by performing a column chromatography. Said chromatographic purification can be performed so that finally a pure diamine-oxidase, i.e. a pure histaminase is recovered or the chromatography can be performed so that the final product is a histaminase which furthermore contains other enzymes. If the chromatographic purification is performed so that a histaminase containing further enzymes is recovered then nevertheless said histaminase containing final product has a histaminase content which is far higher than the histaminase content of the raw enzyme solution which was the starting material of said chromatographic purification process.

EXAMPLE 5

Preparation of the histaminase using a mixed culture of bacteria and yeasts.

In said mixed microorganism culture the yeast strain *Candida crusei* and the lactic acid producing bacteria strain *Lactobacillus bulgaricus* was grown.

The cultivation of said mixed microorganism culture was performed in two fermenters, In both fermenters the cultivation medium was whey.

Before the whey was used as nutrient medium in said process the protein content of the whey was lowered or the proteins were nearly completely removed from the whey. The deproteinized whey or whey with reduced protein content contained about 4.1% of lactose. In the first fermenter, at the beginning of the fermentation, 0.5% of yeast autolysate, referred to the total weight of the whey, were added to the whey.

In the first fermenter and also in the second fermenter, the temperature was kept constant at 44° C. In the first fermenter and also in the second fermenter, the nutrient medium was introduced in such a quantity that 60% of the total volume of said fermenter were occupied by said culture medium. To the first fermenter continuously further whey was added maintaining a steady feed rate. Usually the whey was fed to said first fermenter in a rate of 5 volt.-% of fresh whey per hour, referred to the total volume of whey which is contained in said first fermenter.

In the first fermenter the mixed microorganism culture was grown maintaining a limited supply of air. The supply of air in the first fermenter was adjusted so that the composition of the mixed microorganism culture in the second fermenter was maintained constant, i.e. the ratio of the cells of lactobacillus to the cells of the yeast was maintained constant. Usually said limited air supply to the first fermenter was in the range of 0.30 volumes of air to 0.40 volumes of air per minute per volume of the nutrient medium contained in said first fermenter.

When necessary, to the first fermenter, furthermore, ammonia was added in order to compensate a lowering of the pH-value due to the production of lactic acid by the lactobacillus. The ammonia was added to the first fermenter in such an amount that the pH-value of the nutrient medium in said first germenter was kept constant at 5.5.

Maintaining said cultivation conditions, the bacteria forming lactic acid metabolized all the lactose present in the whey producing lactic acid. Said lactic acid is the carbon source for the yeast strain candida crusei. Said yeast strain further metabolizes said lactic acid forming acetylcoenzyme A which is used for the synthesis.

In said first cultivation phase which is performed in the first fermenter, the yeast present in the culture medium mainly consumes the lactic acid of the culture medium and the yeast, furthermore, consumes as nitrogen source for its protein synthesis the yeast autolysate which has been added to said first fermenter. In said first fermenter, accordingly, the growth of the microorganisms is started.

In the second fermenter the main growth phase, i.e. the essential reproduction of the microorganism cells takes place. In said second fermenter the ammonia is metabolized by the yeast and used for the protein synthesis of the yeast. A part of said ammonia is added to the nutrient medium, i.e. it is added to the first fermenter in order to keep the pH-value in said first fermenter at about 5.5. A further part of the ammonia, however, is formed from histamine present in the culture medium. In the living microorganism cells histaminase is formed and said cells, accordingly, metabolize histamine forming ammonia.

The growth of the yeast, i.e. the reproduction of the yeast cells in the first fermenter is sufficient in order to maintain the composition of the mixed microorganism culture constant, i.e. the ratio of yeast cells to lactobacillus cells. The ammonia supplied to the first fermenter in a quantity to keep the pH-value of the nutrient medium constant at 5.5 makes it possible to maintain constant in said mixed culture the ratio of the cells of lactobacillus to yeast cells.

The second fermenter is as well equipped with a device to monitor the pH-value in the culture medium. Also in the second fermenter the pH-value is kept constant at 5.5. The regulation of the pH-value in said second fermenter, however, is not performed by adding further quantities of ammonia but by controlling the air supply to the first fermenter. Said regulation of the air supply produces a ratio of the intermediate product ammonium lactate to lactic acid which is the optimum ratio for the growth of the yeast.

To the second fermenter continuously the culture medium of the first fermenter which contains the cells of the microorganisms yeast and lactobacillus is added. In said second fermenter the optimum supply of air for the further growth of the microorganisms is maintained.

As soon as a sufficient quanity of microorganisms in the mixed microorganism culture has grown, it is also possible to perform the further cultivation in a single fermenter. Also according to this embodiment of the cultivation a continuous process is preferred. According to said continuous process to the single fermenter continuously fresh whey is added and continuously from the fermenter culture medium containing the cells of lactobacillus and yeast is drawn off.

If the cultivation is performed using two fermenters, then from the second fermenter continuously culture medium containing the yeast cells and lactobacillus cells is drawn off. Said culture medium removed from the second fermenter is immediately centrifuged, preferably according to the process described in example 1.

The mass of cells recovered after the centrifuging is thereafter freed of adhering culture medium, preferably according to the process described in example 1 by suspending the microorganism cells in physiological brine solution and isolating the microorganism cells thereafter by centrifuging.

The raw mass of cells thereafter is either lyophylized and stored according to the process of example 1 or it is submitted to the further purification processes described in the examples 2, 3 and 4.

EXAMPLE 6

Metabolization of histamine in a red wine

The alcoholic fermentation of the musts was performed in the usual way in order to produce a red wine. After the alcoholic fermentation the red wine was separted from the yeast, cooled and to the red wine the raw enzyme product prepared according to example 1 was added in a quantity of 0.01 g/l until 0.5 g/l. The cooled wine was mixed thoroughly and maintained at a temperature of 4° C., optionaly stirring the red wine, until in the red wine no more histamine is detectable. Usually the wine is histamine free after a treatment of 1-10 days. Thereafter the red wine is again filtered in order to remove the added histaminase containing material together with the crude precipitated tartar.

It is advantageous to stir from time to time during the metabolization of the histamine, in order to insure that the oxygen required for said metabolization is introduced into the wine.

EXAMPLE 7

Preparation of a histamine free fresh milk

Pasteurized fresh milk was cooled to a temperature of 4° C. and thereafter to the fresh milk there were added 0.1 g of the raw enzyme product preparted according to example 1 per liter. The fresh milk was maintained at a temperature of 4° C. and stirred from time to time until no more histamine could be detected in the fresh milk.

The so produced histamine free fresh milk was either packed and brought onto the market or to the fresh milk rennet was added in order to produce a milk coagulate. In the latter case the milk coagulate which is used for the production of cheese and, furthermore, also the whey is free of any histamine.

What is claimed is:

1. A process for the preparation of D(—)-amine-oxidase containing material from microorganisms producing it, comprising cultivating D(—)-amine oxidase producing microorganisms selected from the group consisting of *Candida crusei* or lactic acid producing bacteria in a nutrient medium and as soon as a sufficient number of microorganisms have grown, the microorganisms are separated from the culture medium, any remaining culture medium adhering to the microorganisms is removed by washing or by suspending the isolated microorganisms in a liquid medium and the microorganisms are again separated from the liquid medium and thereafter diminuted or crushed to thereby obtain D(—)-amine-oxidase said D(—)-amine-oxidase being capable of degrading histamine in a pH range of about neutral to about 4.

2. Process as claimed in claim 1, wherein the bacteria producing lactic acid are selected from the group lactobacillus.

3. Process as claimed in claim 2, wherein a mixture of microorganisms is cultivated, which mixture contains candida crusei and at least one microorganism selected from the group lactobacillus.

4. Process as claimed in claim 3, wherein the cultivation is performed under conditions in which the lactobacillus metabolizes sugar constituents of the substrate forming lactic acid while the *Candida crusei* metabolizes the produced lactic acid, however does not metabolize the sugar constituents which are present in the nutrient medium.

5. Process as claimed in claim 2 wherein one or more than one microorganism selected from the following groups of microorganism strains is cultivated: *Lactobacillus delbrueckii, Lactobacillus leichmannii, Lactobacillus bulgaricus, Candida crusei.*

6. Process as claimed in claim 3 wherein one or more than one microorganism selected from the following groups of microorganism strains is cultivated: *Lactobacillus delbrueckii, Lactobacillus leichmannii, Lactobacillus bulgaricus, Candida crusei.*

7. Process as claimed in claim 4 wherein one or more than one microorganism selected from the following groups of microorganism strains is cultivated: *Lactobacillus delbrueckii, Lactobacillus leichmannii, Lactobacillus bulgaricus, Candida crusei.*

8. Process as claimed in claim 1 wherein a mixture of the microorganism strain *Lactobacillus bulgaricus* and *Candida crusei* is cultivated.

9. A process as in claim 1, wherein said Ph is in the range of 4–5.

10. Process as claimed in claim 1 wherein the diminuted or crushed microorganisms are dried in vacuo yielding a dry enzyme preparation containing said D(—)-amine-oxidase and wherein said drying operation is performed at a temperature below 7° C.

11. Process as claimed in claim 1 wherein the microorganisms finely diminuted using a homogenizer and the homogenized microorganisms are either extracted using an aqueous extracting solution or from the homogenized microorganisms an aqueous juice is squeezed off and wherein the extract or the juice are dried under vacuum.

12. Process as claimed in claim 11 wherein the extraction with the aqueous extracting solution, respectively the squeezing off of the juice, are performed at a temperature of less than 7° C. and the drying of the extract or the squeezed-off juice is performed at a temperature of less than 7° C.

13. Process as claimed in claim 1 wherein the microorganisms are finely diminuted using a homogenizer and thereafter the homogenized microorganisms are extracted with an aqueous extracting solution the extract applied to a chromatographic column and eluted and the fraction which contains the D(—)-amine-oxidase is dried under vacuum.

14. Process as claimed in claim 13 wherein the homogenized microorganisms are extracted with the aqueous extracting solution at a temperature of less than 7° C. and the eluted fraction which contains the D(—)-amine-oxidase is dried under vacuum at a temperature of less than 7° C.

15. A compound comprising D(—)-amine-oxidase said D(—)-amine-oxidase being capable of degrading histamine in a pH range of about neutral to about 4 prepared according to the process of claim 1.

* * * * *